United States Patent
Bales et al.

(10) Patent No.: US 6,527,938 B2
(45) Date of Patent: Mar. 4, 2003

(54) METHOD FOR MICROPOROUS SURFACE MODIFICATION OF IMPLANTABLE METALLIC MEDICAL ARTICLES

(75) Inventors: Thomas O. Bales, Coral Gables, FL (US); Scott L. Jahrmarkt, Miami Beach, FL (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 09/886,545

(22) Filed: Jun. 21, 2001

(65) Prior Publication Data

US 2002/0198601 A1 Dec. 26, 2002

(51) Int. Cl.$^7$ .............................. C25D 5/48; C25F 3/00
(52) U.S. Cl. .................. 205/229; 205/322; 205/640; 205/675; 205/705; 205/717; 427/2.1; 427/2.24; 427/2.25; 427/2.26; 427/331; 427/343
(58) Field of Search ................... 205/229, 322, 205/640, 657, 675, 705, 706, 717; 427/2.1, 2.24, 331, 343, 431, 2.25, 2.26; 216/100

(56) References Cited

U.S. PATENT DOCUMENTS

| | | | |
|---|---|---|---|
| 2,537,068 A | 1/1951 | Lilliendahl | 75/84 |
| 2,653,869 A | 9/1953 | Gregory | 75/845 |
| 2,834,667 A | 5/1958 | Rostron | 75/0.5 |
| 4,465,561 A | 8/1984 | Nguyen | 205/211 |
| 4,525,250 A | 6/1985 | Fahrmbacher-Lutz | 205/212 |
| 4,923,531 A | 5/1990 | Fisher | 148/126.1 |
| 5,022,935 A | 6/1991 | Fisher | 148/126.1 |
| 5,211,775 A | 5/1993 | Fisher | 148/421 |
| 5,843,289 A | * 12/1998 | Lee et al. | 204/192.3 |
| 5,972,027 A | 10/1999 | Johnson | 623/1 |
| 6,156,459 A | 12/2000 | Negoro | 429/322 |
| 6,405,091 B1 | * 6/2002 | Vachon et al. | 607/120 |

FOREIGN PATENT DOCUMENTS

WO      GB99/01781      6/1999

OTHER PUBLICATIONS

"Direct electrochemical reduction of titanium dioxide to titanium in molten calcium, chloride" by George Zheng Chen et al. in Nature, Sep. 2000.

"Electrochemical method cuts cost of producing titanium", 1 page, published in Advanced Materials & Processes, Dec. 2000.

Thermodynamic Evaluation and Optimization of the LiCl–NaCl–KCl–RbCl–CsCl–$MgCl_2$ $CaCl_2$–$SrCl_2$–System Using the Modified Quasichemical Model Chartrand, P. and Pelton, A.D., in Canadian Metallurgical Quarterly, vol. 39, No. pp 405–420, 2000*.

"Electrochemical method cuts cost of producing titanium", 1 page, published in Advanced Materials & Processes, Dec. 2000.

\* cited by examiner

*Primary Examiner*—Nam Nguyen
*Assistant Examiner*—William T. Leader
(74) *Attorney, Agent, or Firm*—David P. Gordon; David S. Jacobson; Thomas A. Gallagher

(57) ABSTRACT

A process for creating surface microporosity on a titanium (or other metal) medical device includes creating a surface oxide layer on the device; placing the device, which is connected to a negative terminal of an electrical power supply, into a calcium chloride bath; connecting the positive terminal of the power supply to an anode immersed in or containing calcium chloride thereby forming an electrolytic cell; passing current through the cell; removing the device from the bath; and cooling and rinsing the device to remove any surface salt. If necessary, the device is etched to remove metal oxide which may have formed during the cooling process. The resulting device has a microporous surface structure. Alternatively, only a designated surface portion of a medical device is made microporous, either by applying a non-oxidizing mask, removing a portion of the oxide layer, or subtracting a portion of a microporous surface.

37 Claims, No Drawings

METHOD FOR MICROPOROUS SURFACE MODIFICATION OF IMPLANTABLE METALLIC MEDICAL ARTICLES

BACKGROUND OF THE INVENTION

1. Field of the Invention

This invention relates broadly to medical articles and devices. More particularly, this invention relates to methods of treating the surface of the medical article or devices to affect the surface structure thereof, and medical articles and devices having such modified surface structure.

2. State of the Art

Metals and metal alloys, and particularly titanium and titanium alloys, are used for a great variety of implantable articles for medical applications. Among these applications are: structural articles which are used to repair or replace or reinforce bones or to reconstruct joints; structural articles to expand and reinforce arterial, vascular, and other body structures with lumens; wire embolization coils for occluding arteries; enclosures for pacemakers, defibrillators, and implantable infusion pumps; pacing leads; wire sutures and ligatures; staples; filters to catch thrombi and emboli; and, so forth. All implantable articles suffer from some degree of bio-incompatibility, which may be manifested as tissue inflammation, necrosis, hyperplasia, mutagenicity, toxicity, and other reactions, such as attack by giant cells and leukocytes, and macrophages. While titanium and its alloys are generally considered inert when implanted, some biological and biochemical interactions still may occur, and others have found it desirable to provide various coatings on the surface of titanium and titanium alloy implants for certain purposes. The same holds true for many other metals and metal alloys.

In the area of vascular stents others have coated stents (whether made of titanium or other materials) with biological agents (such as genetic material or cellular material) or chemical agents (such as anti-proliferation reagents or cell-growth factors) to reduce problems associated with hyperplasia or inflammation. In order to attach these biological or chemical agents to the surface of a metallic stent, the agents have been mixed with binders such as elastomers or bio-resorbable polymers. These binders can also create problems in that they can cause inflammation, and they can cause the surface of the stent to have more friction, which reduces the ease of stent delivery.

In the field of dental and orthopedic implants, there are sometimes problems associated with acceptance of the implant by body tissues. These problems may be ameliorated by adding anti-inflammatory agents to the surface of the implant. Also, it has been shown that for some implants, it is advantageous for the surface of the implant to be microporous to allow ingrowth of either soft tissue or hard tissue (bone) to enhance the anchoring of the implant in the body. Such microporous surfaces are generally created by attaching a layer of sintered spherical powders to selected surfaces of the implant in areas where tissue ingrowth is desired.

However, attachment of these sintered-powder layers requires additional processing steps, and there is a practical limit to the size of pores that can be achieved. Also, the temperature at which the powders must be sintered approaches the melting point of the material, and the implant is left in a fully-annealed condition, which may be lower in strength than desired. Also, sintered-powder coatings on titanium articles must be applied in a high-temperature, high-vacuum furnace, which is necessarily an expensive and labor-intensive process.

In the field of implanted electrodes, it has been found that sintered powder coatings enhance the attachment of the electrodes and help them to retain a low-impedance connection to the tissue. Such electrodes are generally manufactured by machining an electrode component, applying a multiple-layer coating of powdered metal in an organic binder, and sintering the coated electrode in a controlled-atmosphere (or high vacuum) furnace.

Other medical implants, such as vena-cava filters, aneurism clips, staples, and sutures, are constructed of wire and thus have a relatively large surface area for their size. Accordingly, methods which allow the addition of biological and biochemical agents to the surface of the implant may be advantageous in minimizing the adverse reactions of body tissues with the implant.

Another type of implant, embolization coils, are intended to cause thrombosis so that arteries may be blocked off to mitigate the danger of an aneurism or to deny the blood supply to a tumor. In such devices it may be advantageous to apply biological or chemical agents to the surface of the coils in order to enhance the formation of thrombus.

In the field of arterial stents, coatings have been applied to stainless steel and titanium alloys (e.g., TiNi alloys) to retard tissue reactions such as thrombosis, inflammation, and hyperplasia. Such coatings have been based upon stable bio-compatible polymers (such as styrene-isobutylene-styrene (SIBS)) and bio-resorbable polymers, such as polyglycolic acid. In the work known to date, the active chemical or biological agent is mixed with the polymeric coating material, and the agent then elutes from the coating once the implant is placed in the body.

U.S. Pat. No. 5,972,027 relates to a stent formed of graded layers of powdered metal, with some of the surface layers formed of powder made of larger particle sizes. Once the stent has been sintered, the major portion of the stent is consolidated to a substantially solid form, but that portion of the surface that was made with larger particle-size powder remains microporous. In this way, a stent is manufactured so that at least some parts of the surface are microporous and can be infiltrated with a biological or chemical agent. Such a process is very difficult, since the stent must be made from a "green" preform that is very thin. The finished thickness of an arterial stent ranges from approximately 50 to 125 microns (or approximately 0.002 to 0.005 inches), and the microporous surface layer would be only a fraction of that thickness. Such a thin preform would be very fragile and difficult to handle prior to being sintered.

Other techniques have been described for creating a micro-microporous surface on a metallic article, and such processes might be used for creating a microporous coating on a metallic implant. Such processes include ion milling, photo-chemical machining, electro-discharge machining, and micro-machining using conventional cutting tools.

Of these methods, only the first two are suitable for creating a large number of very small pores (micropores), in the range of 1 to 50 microns in size. Such methods are more suitable for application to flat substrates because they rely on optical or quasi-optical processes. It would be difficult and expensive to apply these processes to small non-flat articles, such as stents, bone screws, dental implants, and clips.

The last three methods are suitable for creating larger pores or pockets in the surface of implants, but such larger pores would require the chemical or biological agent to be bound to the article by means of some binding agent, usually a polymer.

Thus, all of the known methods require either very expensive processes to produce a fine microporous structure, or else it is necessary to use a binding material to attach the biological or chemical agent to the implant article.

SUMMARY OF THE INVENTION

It is therefore an object of the invention to provide a process for modifying the surface of a metal or metal alloy implant to create a microporous surface layer thereon.

It is another object of the invention to provide a process for particularly modifying the surface of a titanium or titanium alloy implant to create a microporous surface layer thereon.

It is a further object of the invention to provide a process for creating a microporous surface on an implant article that could be preferentially applied to only a desired portion of the surface of the implant.

It is also an object of the invention to provide an efficient process which would create a fine microporous structure on the surface of an implant article that would allow a biological or chemical agent to be infiltrated into the surface of the article without the need for binding agents.

In accord with these objects, which will be discussed in detail below, a process for creating a microporous layer on the surface of a titanium or titanium alloy medical device comprises the following steps. The device is cleaned to ensure that it is free of any surface contaminants that could react with and diffuse into the metal when it is heated. A surface layer of titanium oxide or titanium oxy nitride is then created on the surface of the device. According to a preferred reduction process to produce a porous layer at the location of the oxide layer, the oxidized titanium device is placed into a bath of molten calcium chloride and connected to the negative terminal of an electrical power supply. The positive terminal of the electrical power supply is connected to a suitable anode preferably immersed in or containing the molten calcium chloride. An electrical current is then passed through the electrolytic cell. After a time, the titanium device is removed from the molten salt bath, allowed to cool, and rinsed with purified water to remove any surface salt. If necessary, the resulting titanium device may be etched to remove any thin layer of titanium oxide which may have formed during the cooling process. The above described process is suitable where it is desired to modify substantially the entire surface of a medical device.

According to another embodiment, only a designated portion of the surface of a medical device is made microporous. This is done by one of by several techniques. According to a first technique, an area which is not to be treated is masked. The non-masked surface is then subject to oxidation. The remainder of the process is then as described above. According to a second technique, the entire surface of the device is oxidized. The oxidation layer is then selectively removed by etching. The oxide layer is then reduced as described above. According to a third technique, the device may be oxidized and processed through the process as described above so that the entire surface area is made microporous. Then, selected areas of the microporous surface layer may be removed by any subtractive process, such as etching, machining, grinding, etc. With the above techniques, it is possible to produce a titanium or titanium alloy device which has only selected areas of its surface having a microporous structure, and the remaining areas consisting of its base material.

In addition, the processes described can be used on medical devices made of other metal or metal alloy substrate materials. Examples of alternative substrates include reactive and refractory metals, cobalt alloys, nickel alloys, and stainless steel alloys.

Further, other reduction processes can be used to reduce the oxide layer to a metallic layer, including direct reduction by means of an active metal, electrochemical reduction in mixed molten salts, and electrochemical reduction in non-aqueous solvents.

Additional objects and advantages of the invention will become apparent to those skilled in the art upon reference to the detailed description taken in conjunction with the provided figures.

DETAILED DESCRIPTION OF THE PREFERRED EMBODIMENTS

Any of a great variety of titanium or titanium alloy medical articles and devices (hereinafter, collectively "devices") may benefit from a microporous surface layer. Exemplar devices include structural devices which are used to repair or replace or reinforce bones or to reconstruct joints (e.g., hip joint implants, knee joint implants, bone plates and screws, intramedullary nails, etc.); structural devices to expand and reinforce arterial, vascular, and other body structures with lumina (i.e., stents); wire embolization coils for occluding arteries; enclosures for pacemakers, defibrillators, and implantable infusion pumps; pacing leads; wire sutures and ligatures; staples; filters to catch thrombi and emboli; orthodontic implants, archwire, and appliances; and so forth. Examples of such devices are described in the following U.S. Pat. No. 5,868,796 to Buechel et al. entitled "Prosthesis with biologically inert wear resistant surface"; U.S. Pat. No. 6,152,960 to Pappas entitled "Femoral component for knee endoprosthesis"; U.S. Pat. No. 6,077,264 to Chemello entitled "Intramedullary nail for the osteosynthesis of bone fractures"; U.S. Pat. No. 6,096,040 to Esser entitled "Upper extremity bone plates"; U.S. Pat. No. 5,785,712 to Runciman et al. entitled "Reconstruction bone plate"; U.S. Pat. No. 6,048,343 to Mathis et al. entitled "Bone screw system"; U.S. Pat. No. 6,117,157 to Tekulve entitled "Helical embolization coil"; U.S. Pat. No. 5,895,980 to Thompson entitled "Shielded pacemaker enclosure"; U.S. Pat. No. 6,112,118 to Kroll et al. entitled "Implantable cardioverter defibrillator with slew rate limiting"; U.S. Pat. No. 4,103,690 to Harris entitled "Self-suturing cardiac pacer lead"; U.S. Pat. No. 4,901,721 to Hakki entitled "Suturing device"; U.S. Pat. No. 6,071,120 to Birkel entitled "Method and apparatus for ligating orthodontic appliances"; U.S. Pat. No. 5,893,869 to Barnhart et al. entitled "Retrievable inferior vena cava filter system and method for use thereof"; U.S. Pat. No. 5,941,896 to Kerr entitled "Filter and method for trapping emboli during endovascular procedures"; and U.S. Pat. No. 5,725,554 to Simon et al. entitled "Surgical staple and stapler". All of the above patents are hereby incorporated by reference herein in their entireties.

According to the process of the invention, a microporous layer may be created on the surface of such titanium. A titanium medical device is obtained and preferably cleaned to ensure that it is free of any surface contaminants that could react with and diffuse into the titanium when the titanium is heated. This is preferable, as it is well known that contaminants such as organic materials, oxides, metals, halogens, and chalcogenide elements such as sulfur and oxygen will react with titanium and diffuse into it, creating additional phases in the metal and embrittling it. Preferable methods of cleaning include of mechanical polishing, acid etching, and/or electropolishing.

Once the device is cleaned, a surface layer of titanium oxide or titanium oxynitride is created on the device by heating the titanium device in an atmosphere of pure oxygen or a mixture of oxygen and nitrogen. Inert gases such as helium or argon may be added to dilute the oxygen or nitrogen. The preferable temperature range for this oxidization process is 700 to 900° C. By altering the time and temperature of the oxidation process, the thickness of the oxide layer may be controlled. This thickness preferably ranges from a few microns to a few hundred microns. An exemplar range includes approximately 5 to 250 microns.

Alternatively, another process may be used to create the oxidation layer. For example, the titanium device may be oxidized by a chemical solution such as a mixture of hydrofluoric and perchloric acids; by any of the standard vacuum-deposition techniques, such as ion implantation, plasma etching, or chemical vapor deposition, etc; or, by immersion in a suitable electrolyte (such as a potassium hydroxide solution) and passing an electric current therethrough (with the device positive) to create an 'anodized' oxide coating on the device.

The oxidation layer is then reduced (deoxidized). According to a preferred embodiment of reduction, the oxidized titanium device is placed into a salt bath of molten calcium chloride and connected to the negative terminal of an electrical power supply, thereby making the medical device a cathode. The positive terminal of the electrical power supply is connected to a suitable anode, preferably made from either graphite or titanium, immersed in or containing the molten calcium chloride, thereby forming an electrolytic cell. An electrical current is then passed through the electrolytic cell at a current density of approximately 300 milliamperes per square centimeter of cathode area. The current reduces the titanium oxide to titanium, providing a microporosity on the surface structure of the device. Electrolysis preferably occurs at a temperature of 700 to 1000° C. The period of time required to complete the reduction of titanium oxide to titanium, and to extract the diffused oxygen in the base titanium metal, will vary from a few minutes to a few hours. Reduction of metal oxides in this manner is also described in PCT/GB99/01781, entitled "Removal of oxygen from metal oxides and solid solutions by electrolysis in a fused salt" by Fray et al., which is hereby incorporated by reference herein in its entirety.

The titanium device is then removed from the molten salt bath, and allowed to cool. The device is then rinsed clean of any remaining salt, preferably using purified (distilled) water.

The titanium device may be etched, if necessary, to remove any thin layer of titanium oxide which may have formed during the cooling process. A preferred mixture for etching includes hydrofluoric acid (HF) and nitric acid ($HNO_3$). Sulfuric acid may be added to the HF/$HNO_3$ mixture to increase the activity of the etching solution. Alternatively, other etchants such as concentrated carboxylic acids (e.g., oxalic acid or citric acid) may be used. Finally, the etchant is then rinsed from the device.

The resulting implantable medical device has a microporous surface structure which is different, at least on a microscopic scale, than the porous surfaces of the prior art. The microporous surface structure facilitates cell ingrowth and thereby aids in stabilizing the device at its implant location within the body. In addition, the micropores can retain genetic material, cellular material, and biological or chemical agents (e.g., anti-inflammatory agents, anti-proliferation reagents, cell-growth factors) without high-cost sintered powdered layers for biological material or agent retention, or the use (and associated negative reactions) of binders.

According to a second embodiment of the invention, only a designated portion of the surface of a titanium device is surface modified. This may be done by any of several techniques.

According to a first technique, prior to performing the oxidation step of the process, an oxidation-resistant coating that survives the high-temperature oxidation step is applied as a mask to areas of the device where it is desired to not have a microporous surface. Exemplar coatings include a thermally-sprayed coating of calcium chloride, or a plating of gold. Alternatively, the oxidation-resistant coating is applied to the entire surface of the device, and then selectively removed from the areas where it is desired to create a microporous surface. For example, a gold plating may be chemically etched away in selected areas using aqua regia—a mixture of nitric acid (HNO3) and hydrochloric acid (HCl) in an approximately one to three ratio. After the oxidation-resistant coating is applied, the device is subjected to the oxidative step, and the remainder of the process is carried out as described above. It may be desirable to remove the oxidation-resistant coating after the oxidative step, but before the molten-salt bath in order to prevent contamination of the bath or the titanium with decomposed mask material.

According to a second technique, the entire surface of the device is oxidized. The oxidation layer is then removed from selected areas by etching with a suitable etchant, such as a mixture of nitric and hydrofluoric acids. The device is then processed in the molten salt bath as described above.

According to a third technique, the device is oxidized and processed through the process as described above so that the entire surface area is made microporous. Then, selected areas of the microporous surface layer are removed by any subtractive process, such as etching, machining, grinding, etc.

Using any of the above techniques or another suitable technique, it is possible to produce a device with only designated areas of its surface having a microporous structure, and the remaining areas consisting of non-microporous base material.

As it is often desirable to construct medical devices from an alloy of titanium rather than from essentially pure titanium, it is noted devices made of titanium alloys may be similarly processed. Other titanium alloys include: (1) commercially-pure titanium, consisting of titanium plus small amounts of "interstitial" elements, such as carbon, oxygen, and nitrogen, to modify the yield and tensile strength, (2) Ti-6Al-4V (a common implant alloy), (3) titanium and nickel alloy (TiNi, a superelastic/shape-memory alloy), (4) solid-solution titanium alloys, such as Ti—Pt, Ti—Au, Ti—Pd, Ti—Hf, Ti—Nb, and (5) other alloys of titanium, including beta-titanium alloys and alpha-beta alloys. These alloys of titanium have a greater range of stiffness, hardness, yield strength, ultimate tensile strength, machinability, and other properties which may be advantageous in some implant applications, such as orthopedic implants. In such cases, it is possible to perform the process just as described above, or a surface layer of pure titanium may be created on the surface of the device by several different means: (1) the surface may be etched with an etchant which preferably removes other alloying elements, (2) a superficial layer of pure titanium may be added to the device by means of any standard additive process, e.g., plasma deposition, sputtering, physical vapor deposition, chemical vapor deposition, thermal spray, or electroplating; or (3) the device may be made up of a composite material which has a substrate of the desired titanium alloy and a superficial layer of pure titanium.

In addition, while the foregoing process has been described with respect to the production and subsequent reduction of oxide layers on titanium and titanium alloys, these processes are also applicable to other substrate materials. Examples of alternative substrates include: (1) reactive and refractory metals such as zirconium, halfnium, and niobium; (2) cobalt alloys, such as chromium-cobalt-molybdenum alloys (Haynes® 214 and ASTM F75 Cast Alloy) and other cobalt alloys such as MP-35N and Elgiloy®; (3) nickel alloys such as Inconel™; and (4) stainless steel alloys including austenitic alloys such as 304, 316, 317, 321, and 347, martensitic alloys such as 440A, 440B, 440C, ferritic alloys such as 410 and 431, and precipitation-hardening alloys such as 17-4PH, 17-7PH, Custom 455®, Custom 465™, etc.

When using any of the above alternative substrate materials, the thermally-formed oxide layers consist of oxides of the elements comprising the substrate. In the case of pure metals, such as zirconium or halfnium, the oxide layer is a mixture of various oxides of that element. In the case of alloy substrate elements, the oxide layer consists of combined oxides of the substrate elements. For example, 304 stainless steel forms an oxide film of mixed oxides of iron, chromium and nickel. When the mixed oxide films are reduced to form a porous metallic layer, the metal layer resulting from the reduction of the mixed oxides is an alloy of the metallic elements forming the mixed oxide. This alloy is similar in composition to the alloy of the substrate, though there may be a change in composition brought about by differential resistance to oxidation of the alloying elements and by the different reduction potentials of the various metal oxides.

In addition, other reduction processes can be used to reduce the metal oxide layer to a metallic layer, including: (1) direct reduction by means of an active metal, (2) electrochemical reduction in mixed molten salts, and (3) electrochemical reduction in non-aqueous solvents.

With respect to direct reduction, a deoxidant (an alkali metal or alkaline earth metal) in a molten solution with a carrier metal (also an alkali metal or alkaline earth metal) can be used to reduce a refractory or reactive metal such as titanium, zirconium, halfnium, thorium, vanadium, niobium, tantalum, chromium, molybdenum, tungsten, and alloys comprising these metals. See U.S. Pat. No. 4,923,531 to Fisher entitled "Deoxidation of titanium and similar metals using a deoxidant in a molten metal carrier", which is hereby incorporated by reference herein. In Fisher's preferred embodiment, a molten mixture of calcium (the deoxidant) in sodium is used in direct contact with oxidized titanium ($TiO_2$) to reduce the oxide to metallic titanium. In practice, the mixture of molten metals is held in an inert atmosphere and the oxidized article is introduced to the melt and held there for a period of time. Since calcium oxide is more stable than titanium dioxide, the intimate contact of these materials results in a reduction-oxidation reaction in which the titanium dioxide is reduced to titanium metal and the calcium metal is oxidized to calcium oxide. It is noted that Fisher describes a process intended for use primarily with metallic articles of titanium, zirconium, etc., which contain high levels of dissolved oxygen rather than articles having oxide compounds of the metals on their surface. Nevertheless, according to the present invention, if the process is used at a sufficiently high temperature for a sufficiently long reaction time, the oxides reduce to metals. It is also noted that Fisher cites patents which teach the reduction of other oxides (in the form of ores) of titanium, zirconium, etc., to metal. For example, U.S. Pat. No. 2,834,667 to Rostron teaches direct thermal reduction of titanium dioxide by using metallic magnesium at a temperature not substantially less than 1000° C., U.S. Pat. No. 2,537,068 to Lilliendahl et al. teaches the reduction of zirconium oxide or double chloride with calcium at temperatures between 1100° and 1200° C., and U.S. Pat. No. 2,653,869 to Gregory et al. discusses the manufacture of vanadium powder from vanadium trioxide mixed with calcium and calcium chloride at a temperature between 900° and 1350° C. Each of the patents to Rostron, Lilliendahl et al., and Gregory et al. are hereby incorporated by reference herein in their entireties. In addition, in the ancient "thermite" reaction, iron oxide is reacted with metallic aluminum to form metallic iron. Thus, oxygen-contaminated reactive and refractory metals (or their oxides) can be contacted with molten active metals such as calcium and magnesium in order to remove the oxygen and reduce the oxides to pure metals.

Another manner of direct reduction utilizes pure molten alkaline earth metals. U.S. Pat. No. 5,022,935 to Fisher, entitled "Deoxidation of a refractory metal", which is hereby incorporated by reference herein in its entirety, describes the use of pure molten calcium to reduce refractory metals containing oxygen as a contaminant.

Yet another manner of direction reduction uses vapor phase alkaline earth metals. U.S. Pat. No. 5,211,775 to Fisher, entitled "Removal of oxide layers from titanium castings using an alkaline earth deoxidizing agent", which is hereby incorporated by reference herein in its entirety, describes a process in which calcium is used to remove oxygen contamination of titanium articles. In this process the calcium is used in vapor phase. As the calcium vapor reacts with the oxidized or oxygen-contaminated surface of the titanium article, calcium oxide forms on the surface. This oxide is later removed by rinsing or acid pickling.

In view of the foregoing, it will be appreciated that an alkali metal or alkaline earth metal can be used to chemically remove the oxygen which has either been absorbed into or combined with a titanium article. The deoxidizing metal can be used alone as a liquid or in vapor phase, or it may be combined with another metal to form a liquid phase. In the process at least two beneficial actions are achieved. First, oxygen which has been absorbed into a refractory metal, such as titanium, is removed by diffusing out of the refractory metal at a high temperature, and then is chemically bound by the deoxidizing metal (e.g., calcium). Second, non-metallic oxides of the refractory metal or alloy are reduced by direct contact with the deoxidizing metal so that the refractory metal oxides are reduced to the metallic form. In the present invention, both of these actions are important because the metal alloy article has been covered by an oxide and the metal alloy article also has been internally contaminated by oxygen which has diffused into it during the oxidation step. The proposed processes in which a molten deoxidizing metal, such as calcium, is held in contact with the oxidized titanium oxide article resolves both of these conditions: the oxide surface layer is reduced to metal, and the oxygen which has diffused into the titanium alloy is removed by diffusion as it is bound up by the deoxidizing metal.

With respect to electrochemical reduction in mixed molten salts, such mixed molten-salt electrolytic baths may be used in order to achieve lower temperatures than would be possible with pure salts such as calcium chloride. In the preferred reduction process described above, it is necessary for the metallic element whose salt is used to have a higher electrodeposition potential than that required to deoxidize the metal oxides in question. The process works similarly if a sufficiently high potential is used such that the cation of the salt (e.g., calcium) is actually deposited onto the titanium article. In view of the fact that pure calcium may be used to reduce the oxides and remove absorbed oxygen from titanium, it is clear that there is no need to prevent the calcium or other cation from plating out on the titanium article, except that it may necessitate some further cleaning steps after the deoxidation.

If a mixed-salt bath is used in place of pure calcium chloride, it is preferable for the mixed-salt bath to contain at least a substantial portion of the salts which have a high solubility for oxygen. For example, it is preferably that at least one of the following salts be present in the mixed molten-salt bath: $BaCl_2$, CaCl2, CsCl, LiCl, $SrCl_2$, or $YCl_3$. By mixing two or more salts, it is possible to form mixtures which have lower melting points than any of the constituent salts. The mixture of two or more components which forms the minimum melting point is known as the eutectic.

Eutectic mixtures of salts such as LiCl and KCl have been used for this purpose, and in fact it has been shown that titanium may be electrodeposited from such mixtures. See B. N. Popov and H. Wendt, "Electrodeposition of Titanium from Molten Salts," in Emerging Materials by Advanced Processing, Ed. Max-Planck Institut fur Metalforschung, Frankfurt (1988). In addition, extensive work has been done to characterize the thermal and electrochemical properties of such molten-salt mixtures. See "Thermodynamic Evaluation and Optimization of the LiCl—NaCl—KCl—RbCl—CsCl—$MgCl_2$—$CaCl_2$—$SrCl_2$ system Using the Modified Quasichemical Model" Chartrand, P. and Pelton, A. D.; Center for Research in Computational Thermochemistry, Ecole Polytechnique de Montreal.

By using a carefully chosen eutectic mixture (e.g., LiCl—$CaCl_2$ with a melting point of 475° C.) rather than pure $CaCl_2$ (with a melting point 772° C.), it is possible to carry out the deoxidation electrolysis process at a substantially lower temperature. The diffusion rate of oxygen through titanium at 475° C. is expected to be several orders of magnitude slower than at 772° C., as is the rate at which the titanium crystal lattice could re-align itself as the oxygen is removed. Thus, it is expected that at the lower temperature the porous structure of the titanium metallic layer formed by the reduction of the oxide is much finer than it would be if formed at the higher temperature.

Some molten salt baths, e.g., 1-ethyl-3-methyimidazolium chloride-aluminum trichloride molten salt, are liquid at very low temperatures, even below room temperature. Such salt baths may be suitable for electrochemical reduction of thermally formed oxide layers as described here, though it is expected that the rate of reaction will be considerably slower at low temperature. Also, very little dissolved oxygen would be removed from the substrate metal in such as low-temperature process, and a very fine level of porosity is expected because of the limited ability of the titanium or other metal atoms to rearrange at the lower temperature. Nonetheless, such a low-temperature process may be preferable because of its ease of execution and because of the reduced risk of contaminating the base metal, even if only very thin layers of oxide are reduced.

With respect to electrochemical reduction in non-aqueous solvents, non-aqueous electrolytes have been developed for plating of materials whose cations are not stable in aqueous solutions (e.g., aluminum, titanium, calcium, and zirconium) and for use in lithium batteries. Typical electrolytes used in lithium primary cells consist of a lithium salt (usually lithium perchlorate) and an organic solvent in which that salt is soluble, such as propylene carbonate and various ethers. For example, U.S. Pat. No. 4,721,656 to Vance et al. entitled "Electroplating aluminum alloys from organic solvent baths and articles coated therewith", teaches the use of aluminum and lithium chlorides dissolved in anhydrous toluene as an electrolyte for the plating of aluminum alloys. Another example is provided in U.S. Pat. No. 4,525,250 to Fahrmbacher-Lutz et al., entitled "Method for chemical removal of oxide layers from objects of metal", which teaches the use of a methanol-based electrolyte containing hydrogen fluoride and one or more alkali fluorides and/or ammonium fluoride for the removal of titanium oxides from articles of titanium. Yet another example is provided in U.S. Pat. No. 4,465,561 to Nguyen, et al., entitled "Electroplating film-forming metals in non-aqueous electrolyte", which teaches the use of toluene and para-xylene as solvents for electrolytes for plating metals which cannot be plated in an aqueous environment. A further example is provided in U.S. Pat. No. 6,156,459 to Negoro et al., entitled "Nonaqueous-electrolytic solution secondary battery", which teaches the use of aprotic organic solvents, such as propylene carbonate, ethylene carbonate, butylene carbonate, dimethyl carbonate, diethyl carbonate, methyl ethyl carbonate, .gamma.-butyrolactone, methyl formate, methyl acetate, 1,2-dimethoxyethane, tetrahydrofuran, 2-methyltetrahydrofuran, dimethyl sulfoxide, 1,3-dioxolane, formamide, dimethylformamide, dioxolane, dioxane, acetonitrile, nitromethane, ethyl monoglyme, phosphoric acid triesters, trimethoxymethane, dioxolane derivatives, sulfolane, 3-methyl-2-oxazolidinone, propylene carbonate derivatives, tetrahydrofuran derivatives, ethyl ether, and 1,3-propanesulfone (preferably ethylene carbonate and propylene carbonate) as non-aqueous solvents for electrolytes in lithium batteries. Each of the patents in the above examples is hereby incorporated by reference herein in their entireties.

As in the foregoing applications to electroplating and lithium battery chemistry, non-aqueous solvents which have the power to dissolve alkali metal and alkaline-earth metal halides and haloxides (e.g., LiCl, $CaCl_2$, $LiClO_4$) are suitable for the electrochemical reduction of oxides of metals such as titanium, zirconium, nickel, chromium, and iron. Thus, electrolytes consisting of salts such as calcium chloride and lithium perchlorate dissolved in solvents such as propylene carbonate are applicable for treating thermally-formed oxide surface layers on titanium substrates so that the oxide layers are reduced to porous metal layers.

It should be noted that if a low-temperature process is used to reduce the oxide layer to metal, a relatively small amount of oxygen that might have been dissolved into the metal substrate would be removed during the electrochemical reduction process. Since the removal of dissolved oxygen is dependent upon the ability of oxygen to diffuse out of the metal substrate, it is expected that when the reduction process is carried out at low temperatures, such as at room temperature, very little of the dissolved oxygen in the substrate titanium would be removed. This limited elimination of oxygen would likely result in reduced ductility in the titanium (or other metal) article. As such, if the medical device article is relatively thin or if the article is subject to bending after the reduction process (or in use), the remaining dissolved oxygen would likely be deleterious.

There have been described and illustrated herein several embodiments of processes for surface treating metal and metal alloy medical devices, and particularly surface treating titanium and titanium alloy medical devices. While particular embodiments of the invention have been described, it is not intended that the invention be limited thereto, as it is intended that the invention be as broad in scope as the art will allow and that the specification be read likewise. Thus, while particular titanium alloys have been disclosed, it will be appreciated that other titanium alloys may be used as well. In addition, while particular oxidation and etchant processes are disclosed, it will be appreciated that other types of such processes can be used. Also, while several methods for reduction have been disclosed, it will be appreciated that yet other such methods can be used. Furthermore, while several methods have been disclosed for reducing only portions of a metal or metal alloy device, yet other methods can be used. Moreover, while particular medical devices made of metal or metal alloys have been disclosed, it will be appreciated that other medical devices made of metal or metal alloys can be thusly treated. It will therefore be appreciated by those skilled in the art that yet other modifications could be made to the provided invention without deviating from its spirit and scope as claimed.

What is claimed is:

1. A method of surface treating a medical device, comprising the steps of:
   a) obtaining a medical device made at least partially of titanium;
   b) oxidizing a treating surface of said medical device; and
   c) electrolyzing said medical device with said oxidized treating surface in a bath of molten calcium chloride for a period of time such that a microporosity is provided on said treating surface of said medical device.

2. A method according to claim 1, wherein:
   said step of electrolyzing includes,
      connecting the medical device to a negative terminal of an electric power supply such that the medical device defines a cathode, and connecting a positive terminal to an anode immersed in or containing the calcium chloride, thereby forming an electrolytic cell, and passing a current through the electrolytic cell.

3. A method according to claim 2, wherein:
   said anode is made from one of graphite or titanium.

4. A method according to claim 2, wherein:
   said current is passed through said electrolytic cell at a current density of approximately 300 milliamperes per square centimeter of cathode area.

5. A method according to claim 1, further comprising:
   d) before said oxidizing step, cleaning said medical device.

6. A method according to claim 5, wherein:
   said step of cleaning is done by way of at least one of mechanical polishing, acid etching, and electropolishing.

7. A method according to claim 1, wherein:
   said step of oxidizing includes placing said medical device in an atmosphere of one of pure oxygen, a mixture of oxygen and nitrogen, a mixture of oxygen and an inert gas, and a mixture of oxygen, nitrogen and an inert gas.

8. A method according to claim 1, wherein:
   said step of oxidizing occurs at 700 to 900° C.

9. A method according to claim 1, wherein:
   said step of oxidizing creates an oxidized layer between approximately 5 and 250 microns thick on said treating surface.

10. A method according to claim 1, wherein:
    said step of oxidizing includes at least one of applying a chemical solution to the medical device, depositing an oxidized layer by vacuum-deposition to said medical device, and immersing said medical device in a suitable electrolyte and passing a electric current through the device.

11. A method according to claim 10, wherein:
    said step of oxidizing is performed by applying a chemical solution, and said solution is a mixture of hydrofluoric and perchloric acids.

12. A method according to claim 10, wherein:
    said step of oxidizing is performed by vacuum-deposition by one of ion implantation, chemical vapor deposition and physical vapor deposition.

13. A method according to claim 1, further comprising:
    d) after electrolysis, removing said medical device from said calcium chloride; and
    e) rinsing said calcium chloride from said medical device.

14. A method according to claim 1, further comprising:
    d) cooling said medical device thereby forming a titanium oxide layer on said treating surface
    e) etching said treating surface with an etchant to remove said titanium oxide layer; and
    f) rinsing said etchant from said treating surface.

15. A method according to claim 14, wherein:
    said etchant includes one of
       (i) a mixture of hydrofluoric acid and nitric acid,
       (ii) a mixture of hydrofluoric acid, nitric acid, and sulfuric acid, and
       (iii) concentrated carboxylic acids.

16. A method according to claim 1, further comprising:
    d) providing at least one of cellular material and genetic material in said microporosity.

17. A method according to claim 1, further comprising:
    d) providing a chemical or biological agent in said microporosity.

18. A method according to claim 1, wherein:
    said medical device is made from a titanium alloy.

19. A method according to claim 18, further comprising:
    d) prior to said step of oxidizing said treating surface, applying a layer of pure titanium on said treating surface of said medical device.

20. A method according to claim 1, wherein:
    said treating surface is less than a total surface of said medical device.

21. A method according to claim 20, further comprising:
    d) prior to said step of oxidizing said treating surface, applying an oxidation-resistant coating to said total surface surrounding said treating surface.

22. A method according to claim 20, further comprising:
    d) prior to said step of oxidizing said treating surface, applying an oxidation-resistant coating to said total surface; and
    e) selectively removing said oxidation-resistant coating from said total surface surrounding said treating surface.

23. A method according to claim 1, wherein:
    a portion of said microporosity is removed from said treating surface.

24. A method according to claim 1, wherein:
    said medical device is one of
       (i) a bone implant,
       (ii) a bone replacement, (iii) a structural device which expands and reinforces arterial, vascular, or other body structures,
(iv) a wire embolization coil,
(v) an enclosure for a pacemakers, a defibrillator, or an implantable infusion pump,
(vi) a pacing lead,
(vii) a wire suture or ligature,
(viii) a surgical staple,
(ix) a filter to catch thrombi and emboli, and
(x) an orthodontic implant or appliance.

25. A method of surface treating a medical device made at least partially from a metal, comprising:
  a) obtaining the medical device made at least partially from the metal;
  b) oxidizing a surface of said medical device to form an oxide layer thereon;
  c) removing a portion of said oxide layer from a portion of said surface; and
  d) reducing said surface of said medical device having said oxide layer to form a microporosity at said surface.

26. A method according to claim 25, wherein:
said step of reducing includes electrolyzing said medical device in a bath of molten calcium chloride for a period of time.

27. A method according to claim 25, wherein:
said metal is titanium.

28. A method of surface treating a medical device, comprising:
  a) obtaining a medical device made at least partially from titanium and having an oxide layer at least partially over a surface thereof; and
  b) removing at least a portion of said oxide layer by electrolysis of said medical device in a fused salt such that oxygen from said oxide layer dissolves in said fused salt to form a microporosity in said surface.

29. A method according to claim 28, wherein:
said fused salt is calcium chloride.

30. A method according to claim 28, further comprising:
  c) providing at least one of cellular material and genetic material in said microporosity.

31. A method according to claim 28, further comprising:
  c) providing a chemical or biological agent in said microporosity.

32. A method according to claim 28, wherein:
said medical device is made from a titanium alloy.

33. A method of surface treating a medical device, comprising:
  a) obtaining a medical device made at least partially from metal and having an oxide layer at least partially over a surface thereof; and
  b) removing at least a portion of said oxide layer by reduction of said oxide layer to form a microporosity in said surface.

34. A method according to claim 33, wherein:
said reduction is performed by a method selected from the group of,
  i) direct reduction by means of an active metal,
  ii) electrochemical reduction in mixed molten salts, and
  iii) electrochemical reduction in a non-aqueous solvent.

35. A method according to claim 33, wherein:
said metal is selected from the group of,
  i) titanium and titanium alloys,
  ii) reactive metals and refractory metals,
  iii) cobalt alloys,
  iv) nickel alloys, and
  v) stainless steel alloys.

36. A method according to claim 33, further comprising:
  c) providing at least one of cellular material and genetic material in said microporosity.

37. A method according to claim 33, further comprising:
  c) providing a chemical or biological agent in said microporosity.

* * * * *